United States Patent [19]

Lee et al.

[11] Patent Number: 5,318,501
[45] Date of Patent: Jun. 7, 1994

[54] LINEAR MOTION, MUSCLE-ACTUATED CARDIAC ASSIST DEVICE

[75] Inventors: Philip H. J. Lee, Woodbury; Michael Colson, Minneapolis; Kendra Gealow, Minnetonka, all of Minn.

[73] Assignee: Medtronic, Inc., Minneapolis, Minn.

[21] Appl. No.: 950,868

[22] Filed: Sep. 24, 1992

[51] Int. Cl.5 ............................................. A61M 1/12
[52] U.S. Cl. ............................................. 600/16; 623/3
[58] Field of Search ................ 600/16, 17, 18; 623/3

[56] References Cited

U.S. PATENT DOCUMENTS

| | | | |
|---|---|---|---|
| 4,453,537 | 6/1984 | Spitzer | 600/17 |
| 4,685,446 | 8/1987 | Choy | 600/18 |
| 5,006,104 | 4/1991 | Smith et al. | 600/16 |
| 5,169,381 | 12/1992 | Snyders | 600/16 |
| 5,171,207 | 12/1992 | Whalen | 600/16 |

Primary Examiner—William E. Kamm
Assistant Examiner—Kennedy J. Schaetzle
Attorney, Agent, or Firm—Gregory P. Gadson; Harold R. Patton

[57] ABSTRACT

A linear motion, muscle-actuated cardiac assist device novelly uses a powering muscle whose contractions and relaxations are made in a substantially linear fashion, as opposed to the curvilinear muscle motions associated with prior art muscle-actuated cardiac assist devices. As a result, collateral circulation of the powering muscle need not be cut, theoretically leading to prevention of ischemia in the powering muscle. Other benefits include: greater energy efficiency of the powering muscle; greater available choice of powering muscles (i.e., not limited to the latissimus dorsi as the powering muscle); and reduced profile height of the cardiac assist device to reduce protrusion from the implanted area of the body.

6 Claims, 8 Drawing Sheets

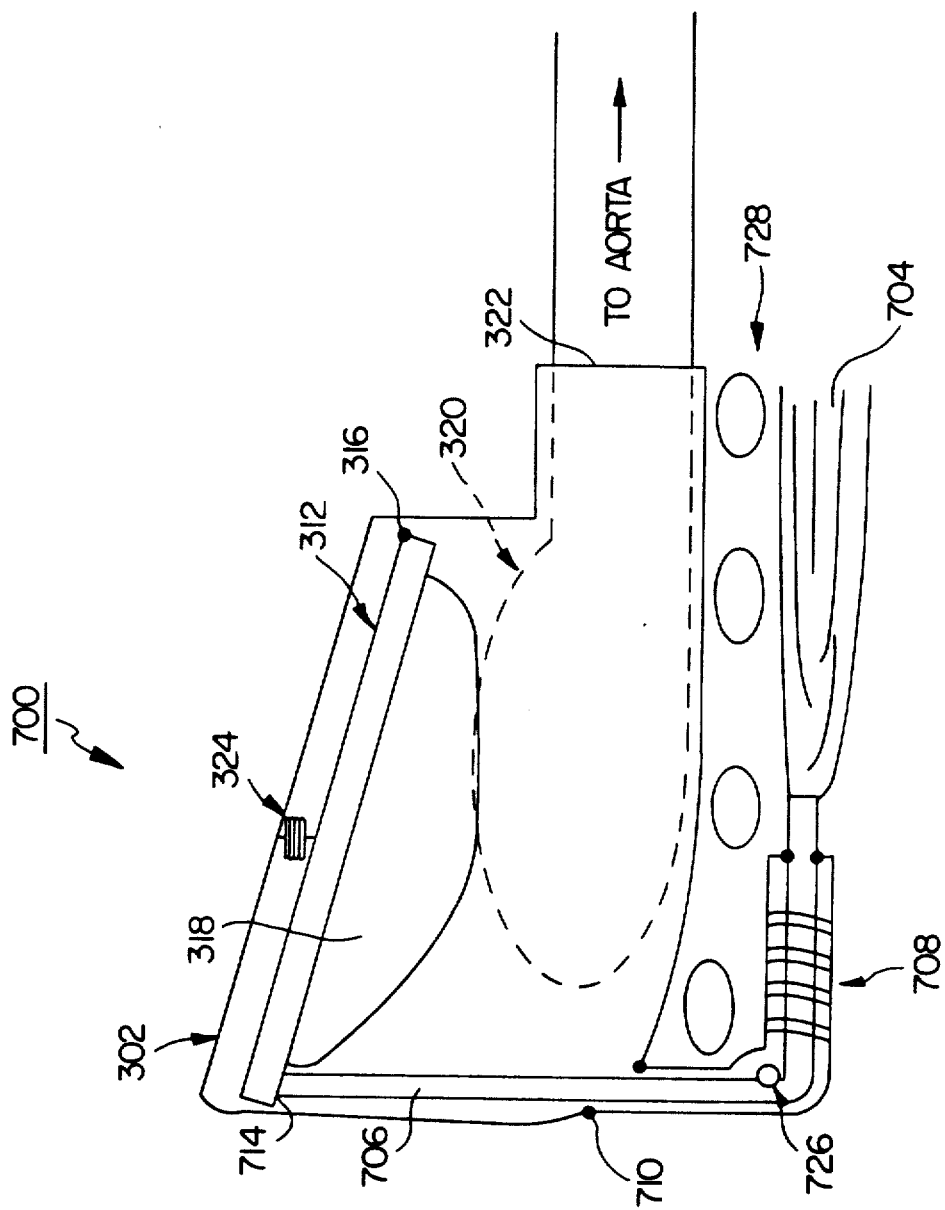

LINEAR MOTION, MUSCLE-ACTUATED CARDIAC ASSIST DEVICE

FIELD OF THE INVENTION

The present invention generally relates to cardiac assist devices, and more particularly to muscle-powered cardiac assist devices.

BACKGROUND OF THE INVENTION

Muscle-powered cardiac assist systems such as the one labeled 100a in FIG. 1A have been developed to aid patients with chronically and unacceptably low cardiac output, and who cannot have their cardiac output raised to acceptable levels by traditional treatments such as drug therapy. (See G. L. Anstadt & W. E. Britz, Jr., *Continued Studies in Prolonged Circulatory Support by Direct Mechanical Ventricular Assistance*, 14 Trans. Amer. Soc. Artif. Int. Organs 297 (1968)). In such a system 100a the ventricles of a heart 102a are surrounded by a pneumatic cardiac cup 104a to assist the heart 102a (and thus raise caridac output) during scheduled contractions. During the systolic (contraction) phase of the cardiac cycle the cardiac cup 104b, made of a flexible membrane, is inflated by a fluid to increase external pressure upon the ventricles, thus causing them to contract to a greater degree than otherwise. During the diastolic (relaxation) phase of the cardiac cycle the cardiac cup 104a is deflated to reduce the external pressure upon the ventricles, allowing them to expand to their at-rest position. In usual practice the cardiac pump is coupled to an external air (working fluid) source that drives a diaphragm (not shown) within the cup 104a.

As a variation on this theme, muscle tissue can be used to provide power to drive the working fluid. This is accomplished in FIG. 1A by coupling a cardiac pump to a balloon 114a that is wrapped by muscle tissue 116a. The muscle tissue 116a is stimulated to contract (via leads 132a) by an implantable pulse generator (IPG) 128a that senses the cardiac cycle, usually from heart electrocardiogram (ECG) activity via a cardiac sensing electrode 130a. This mode of assist is in co-pulsation with the heart pumping action.

Another cardiac assist device has been disclosed by Nielson and Chiu, in the book *Biomechanical Cardiac Assist Cardiomyoplasty and Muscle-Powered Devices*, edited by Ray C. J. Chiu, Futura Publishing Co., Inc., Mount Kisco, 1986 pp. 141-150, which book is hereby incorporated by reference.

The cardiac assist system 100b in FIG. 1B is similar to that of FIG. 1A, but has an aortic blood pump 126b (which is coupled to the aorta 134b) instead of the cardiac cup 104a. The aortic blood pump 126b provides hemodynamic and cardiac assist according to a principle of operation not unlike a prior art temporary intra-aortic balloon pump. As with the cardiac cup 104a, the aortic blood pump 126b must be coupled to an outside, fluid-pumping source, either external to the body or alternatively to a fully implantable system powered by a muscle pump that contracts in response to stimulation emanating from an IPG.

In operation of the system in FIG. 1B, the IPG 128b senses the onset of the diastolic phase via the sensor lead 130b, and stimulation bursts are supplied via the stimulator leads 132b to the powering muscle tissue 116b. The stimulation bursts cause the muscle tissue 116b to contract and thus cause the balloon 114b to expel working fluid, which then causes a diaphragm (not shown) in the aortic blood pump 126b to inflate. Somewhat before the onset of the systolic phase, the muscle tissue 116b is allowed to relax, causing the diaphragm in the aortic blood pump 126b to deflate, which causes a sudden increase in vascular space, and an easing of the load the heart 102b must pump against. This mode of assist is in counter-pulsation with the heart pumping action.

The systems 100a and 100b have some disadvantages related to the use of the balloon pumps 114a and 114b, which are, inter alia, wrapping the muscle tissue 116a and 116b around the balloon pumps 114a and 114b necessitates cutting the muscle collateral circulation, which may eventually lead to ischemia followed by the death of the tissue. Further, because the surface area of the powering muscle tissue is more than adequate to cover the surface area of the balloon pumps, excess muscle which overhangs the balloon pumps tends to generate unwanted tangential forces on the balloon pumps during muscle contraction, thereby wasting available energy of the powering muscle tissue. Also, such arrangements 100a and 100b are typically only well-suited for the latissimus dorsi muscle, and are not practical for other skeletal muscles. Additionally, the shape and size of the balloon pumps 114a and 114b usually result in undesirably large protrusions from the implanted area of the body.

SUMMARY OF THE INVENTION

The following are objects of the present invention in view of the above.

A first object of the present invention is to provide a muscle-powered cardiac assist device wherein the powering muscle moves in a more natural motion.

A second object of the present invention is to provide a muscle-powered cardiac assist device which prevents the development of ischemia in the powering muscle.

A third object of the present invention is to provide a muscle-powered cardiac assist device having greater efficiency of the energy expended by its powering muscle.

A fourth object of the present invention is to provide a muscle-powered cardiac assist device which is compatible with different types of powering muscles.

A fifth object of the present invention is to provide a muscle-powered cardiac assist device with reduced protrusion from the area of the body implanted with said device.

There is provided in accordance with the present invention, a muscle-powered cardiac assist device for use in a cardiac assist system, the cardiac assist device at least including:

a flexible fluid chamber having working fluid therein;

fluid chamber support means for supporting the flexible fluid chamber;

fluid chamber contraction means coupled to the flexible fluid chamber and to the fluid chamber support means for contracting the flexible fluid chamber to cause working fluid to further power the cardiac assist system; and linear muscle coupling means for coupling powering muscle tissue to the fluid chamber contraction means, so that substantially linear motion of the powering muscle tissue powers the fluid chamber contraction means.

The details of the present invention will be revealed in the following description with reference to the attached drawing.

BRIEF DESCRIPTION OF THE DRAWING

The various figures of the drawing are briefly described as follows:

FIG. 7 is a side view of a third version of the second embodiment of the present-inventive cardiac assist device, which version is optimized for use with the latissimus dorsi as the powering muscle.

Figure 1A:
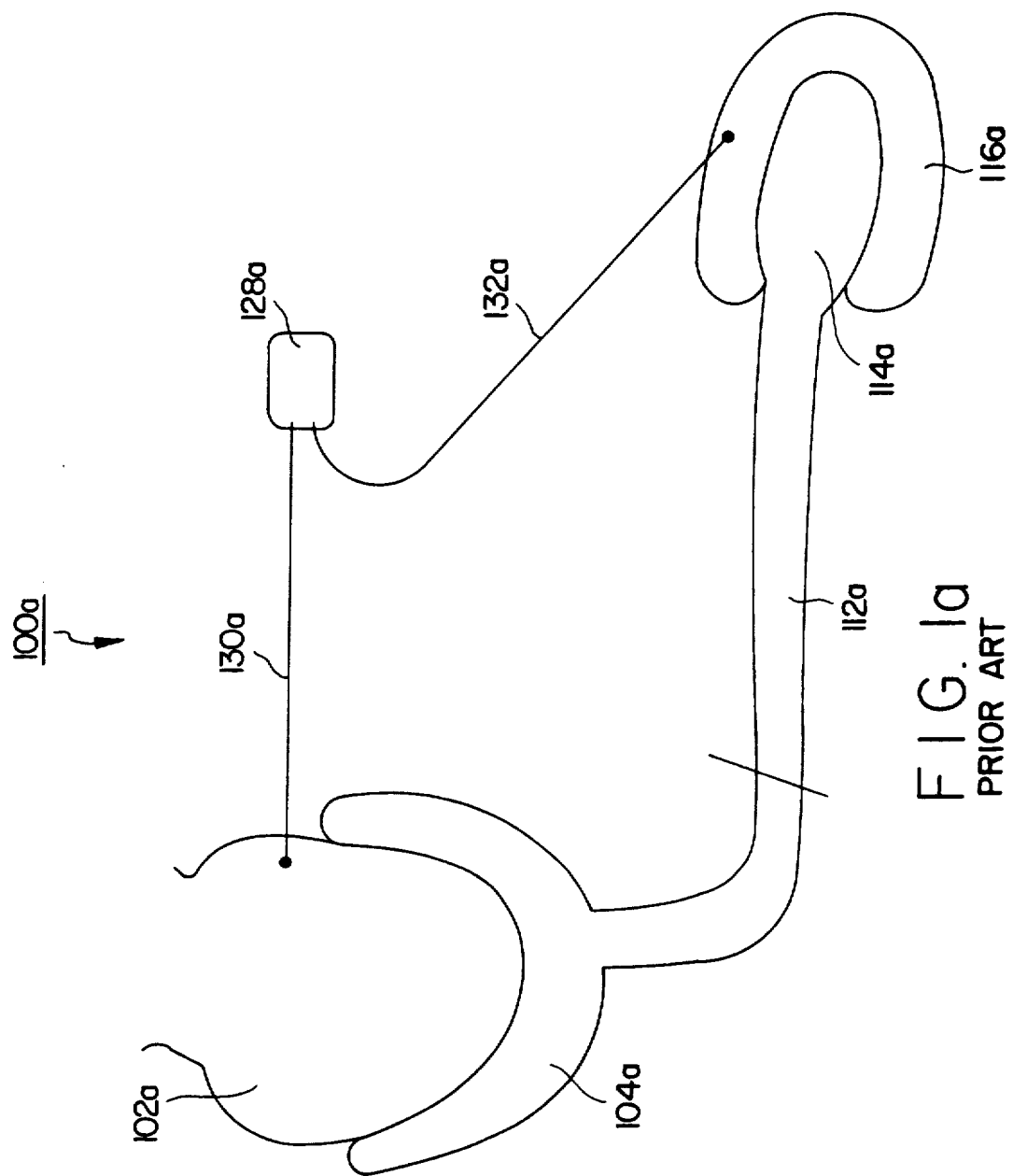
FIG. 1A is a schematic diagram of a prior art muscle-powered cardiac assist system having a cardiac cup.

The elements shown in the drawing figures and described infra. are numbered such that the leftmost digit corresponds to the drawing figure in which an element first appears.

DETAILED DESCRIPTION OF THE PREFERRED EMBODIMENTS

Figure 1B:
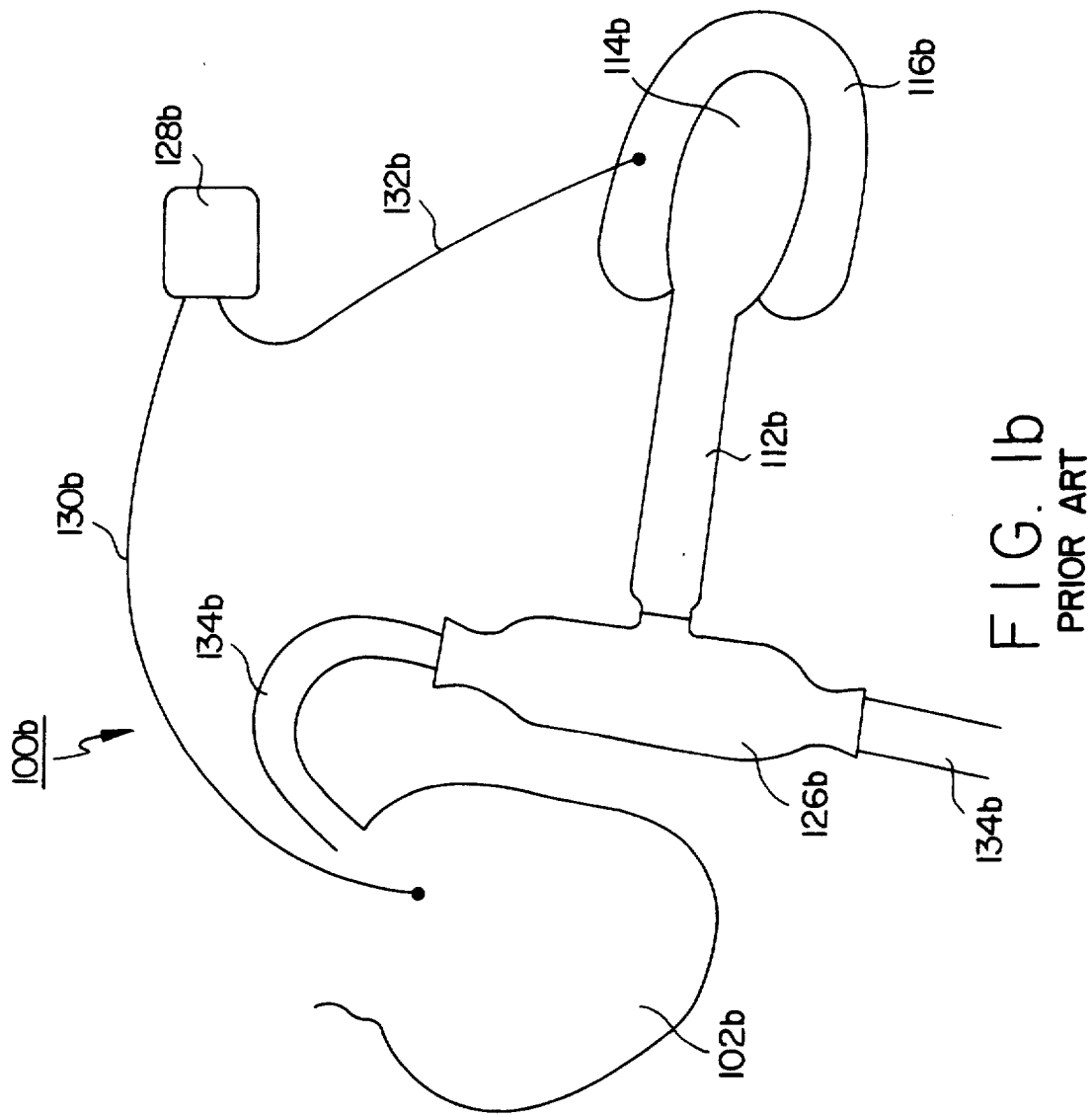
FIG. 1B is a modified version of the diagram in FIG. 1A having an aortic blood pump in place of the cardiac cup.

The present invention is a cardiac assist device capable of subsuming the functions of the balloon pumps 114a and 114b in FIGS. 1A and 1B, but is not limited to use with such systems. The present-inventive cardiac assist device is powered by muscle tissue which contracts to cause working fluid to act on another device (e.g., a blood pump, a cardiac cup, an aortic valve, or other assist device) or directly upon a portion of a cardiac system to help improve the cardiac function. A first embodiment of a linear muscle-powered cardiac assist device 200 shown in FIG. 2 can replace the balloon pumps 114a and 114b in FIGS. 1A and 1B, or can function in other cardiac assist systems. The cardiac assist device 200 is powered by the linear motion (contraction and relaxation) of the powering muscle tissue 228; i.e., unlike prior art muscle-powered cardiac assist devices where the muscle motion is circular or transverse to the longitudinal axis of the muscle, the motion of the powering muscle is substantially along its longitudinal axis, or linear in nature. Although optimally designed to be mounted subcutaneously and pump non-blood working fluid, it is possible to place the cardiac assist device 200 intrathoracicly, and it is also possible for the cardiac assist device 200 to pump blood directly.

A metal housing 202 (titanium in the preferred embodiment) houses a movable plate 204 which pivots at one end around a fulcrum 206, and a balloon chamber or bladder 208 for handling working fluid between the movable plate 204 and a support wall 210 of the housing. The fulcrum 206 may be spring-loaded, so that the stored energy of the spring retracts the movable plate during relaxation of the powering muscle tissue 228 (described infra.). The working fluid may be air or another suitable fluid, and may even be blood in a specially designed system in which the device 200 is directly coupled to the body's blood circulation. The balloon chamber 208 has an orifice 212 protruding through an opening 214 in the housing, which orifice 212 is connectable to the likes of conduits 112a and 112b in FIGS. 1A and 1B. The orifice 212 serves to expel higher pressurized working fluid during compression of the balloon chamber 208, and admit lower pressurized working fluid during expansion of the balloon chamber 208.

In the preferred embodiment the orifice 212 can serve as a convenient securing means for the device 200 when lodged between two of a patient's skeletal ribs 216. Suture holes can be added to the housing 202 for fastening other portions of the housing 202 to the ribs 216.

Figure 2:
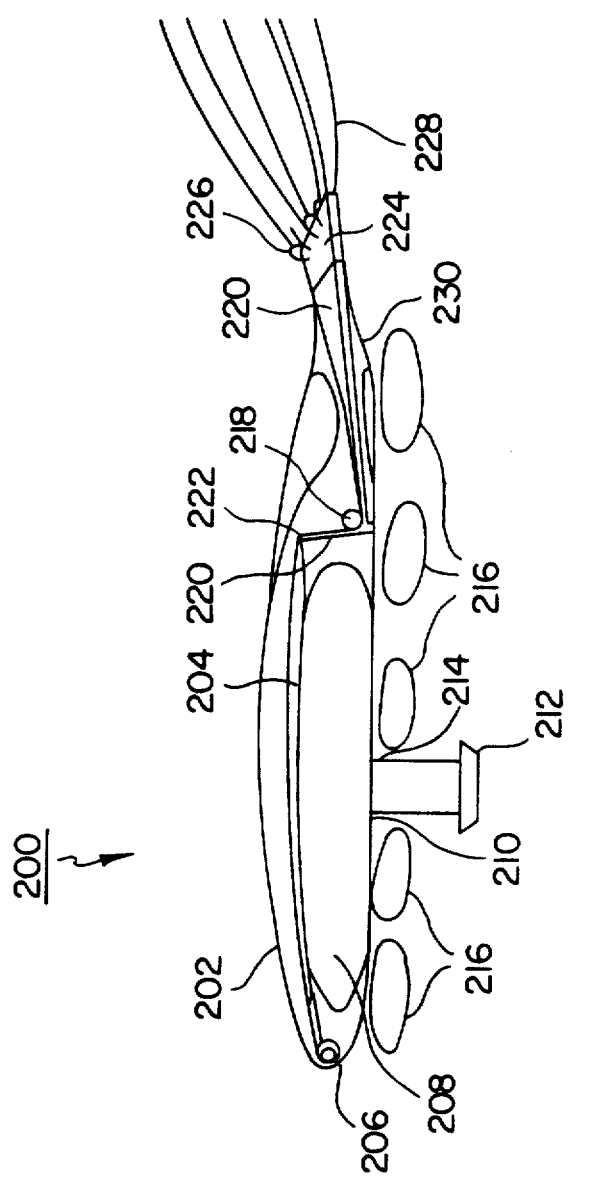
FIG. 2 is a side view of the first embodiment of the present-inventive cardiac assist device.

A connecting member 220—preferably thin, fiber-reinforced and rubberized—connects the powering muscle tissue 228 to the movable plate 204 at a point of attachment 222. A rotating dowel 218 rotatably connected at its ends to the walls of the housing 202 is used to tautly deflect the connecting member 220 from an orientation parallel with the motion plane of the powering muscle tissue 228 to an orientation allowing for efficient displacement of the movable plate 204. In FIG. 2, for example, the connecting member 220 is substantially horizontal along the portion closest to the powering muscle tissue 228, and substantially vertical along the portion closest to the connecting point 222. A special connecting member tip 224 is made of a material more suitable to suturing, and in fact is sutured to the powering muscle tissue 228 with sutures 226.

The connecting member 220 is not only used to couple the powering muscle tissue 228 to the movable plate 204, but in combination with the rotating dowel 218, the connecting member 220 transforms the resultant force vectors created by the powering muscle tissue 228, to have a different direction with the same magnitude. For example, in FIG. 2 the resultant forces created by the motion of the powering muscle tissue 228 are substantially in the horizontal direction, but they are converted, through the elbow shape of the connecting member 220 to forces of the same magnitude which act on the movable plate 204 in a substantially vertical direction. This allows the powering muscle tissue 228 to compress and expand the balloon chamber 208 by linear motion alone—the natural motion of many muscles, including those of the skeletal type. Thus, the prior art practice of wrapping the powering muscle around the balloon chamber (or equivalent) and the negative consequences previously mentioned are avoided.

A thin, flexible bio-compatible polymer cover 230 is applied to a portion of the housing 202 and the connecting member 220 to hermetically seal the metal housing 202 and hence the cardiac assist device 200, while still permitting flexibility in the connecting member 220.

Figure 3:
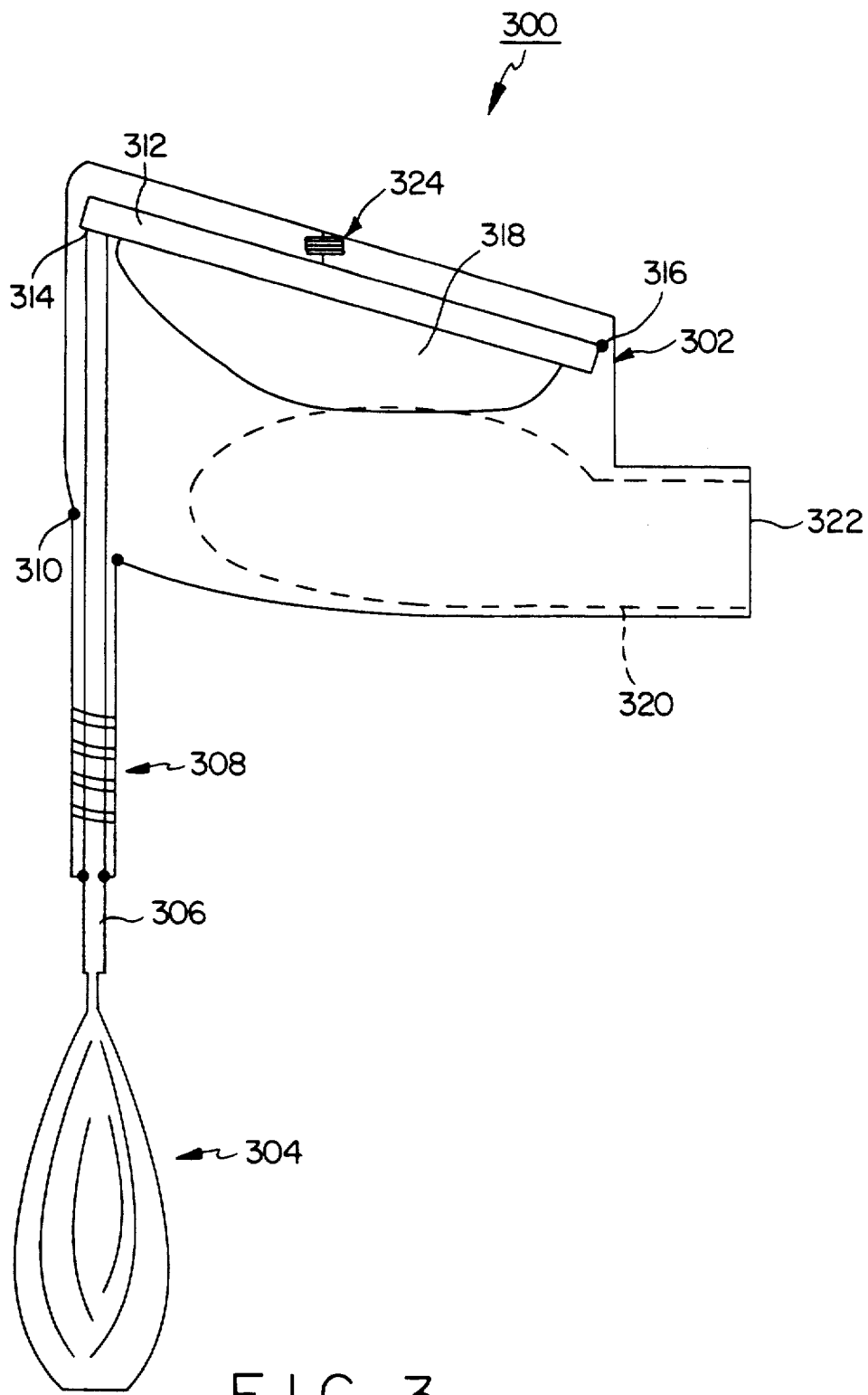
FIG. 3 is a side view of a first version of the second embodiment of the present-inventive cardiac assist device during cardiac systole.

A first version of a second embodiment 300 is shown in FIG. 3. The cardiac assist device 300 is optimally designed to pump blood (thus it is "circular"), but the fluid pumped need not be limited to blood. By directly coupling the powering muscle to a blood pump the cardiac assist device 300 avoids the power losses associated with non-direct or indirect-coupled (with respect to blood pumps) cardiac assist devices, such as the one 200 in FIG. 2. The housing 302, made of a rigid or semi-rigid material and ideally impermeable, houses a bladder or diaphragm 320 which handles the working fluid. In the preferred embodiment, the material of the diaphragm 320 is the same as that of the inside walls of the housing 302. The walls of the diaphragm are dimensioned such that during compression, the diaphragm forms, with the help of a cam-shaped compression plate 318, a desirable shape (see FIG. 4) to avoid thrombogenic blood flow patterns inside the diaphragm.

Powering muscle tissue 304 is linearly connected at an end to a rigid connecting member 306. A portion of the connecting member 306 is slidably located in an extension section 308, and enters the housing via a housing opening 310. The extension section 308 is sealed (by using a flexible material bonded to both the opening and the connecting member) at the end nearest the powering muscle tissue 304 to prevent infiltration of the housing 302 by body fluids. The connecting member 306 is also connected at a hinged connection point 314 to a rigid swivel plate 312. The swivel plate 312 is connected at another point 316 to a dowel or similar member which allows rotation of the swivel plate 312 around the point 316. A compression member 318 generally in the shape of a cam is attached to the swivel plate 312 as shown, and touches the surface of the diaphragm 320 without displacing the walls of the diaphragm during cardiac systole, the condition present during the configuration in FIG. 3. In this embodiment the powering muscle tissue 304 is relaxed during cardiac systole, awaiting the cardiac diastolic phase.

Figure 4:
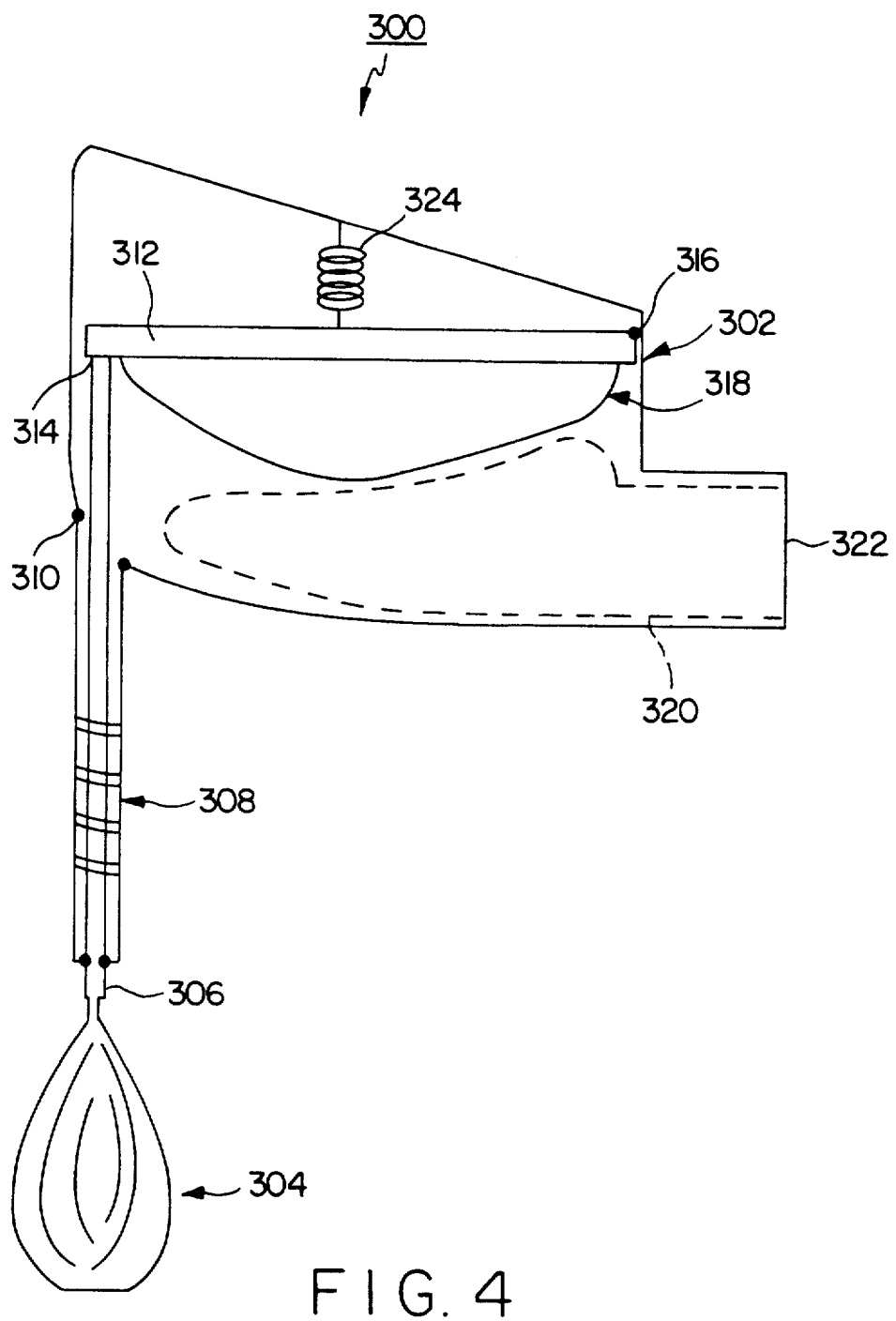
FIG. 4 is a side view of a first version of the second embodiment of the present-inventive cardiac assist device during cardiac diastole.

During cardiac diastole, the components of the cardiac assist device 300 move to the positions shown in FIG. 4. During this phase the powering muscle tissue 304 is stimulated to contract in manner known in the art. The contraction of the muscle tissue 304 pulls down the connecting member 306, which in turn pivots the free end of the swivel plate 312 to the lower position shown.

Downward swiveling of the swivel plate causes the compression member to efficiently compress the diaphragm 320, thus expelling working fluid from a fluid port 322. A return spring 324 is attached to the upper inside wall of the housing 302 and the swivel plate 312. The return spring 324 is shown in an expanded state in FIG. 4. During the cardiac systolic phase, the spring action of the return spring 324 pulls the swivel plate and hence the compression member 318 back to the resting positions depicted in FIG. 3 to aid the filling of the diaphragm 320 and thus add hemodynamic benefits. The magnitude of the moment around the swivel point 316 caused by the return spring 324 is lower than the magnitude of the moment around the swivel point 316 caused by the resultant force of the powering muscle tissue 304. Swiveling the compression member 318 upward in FIG. 4 during cardiac systole allows the diaphragm 320 to return to its shape as shown in FIG. 3, and restore the increased volume of working fluid associated with cardiac diastole.

Figure 5:
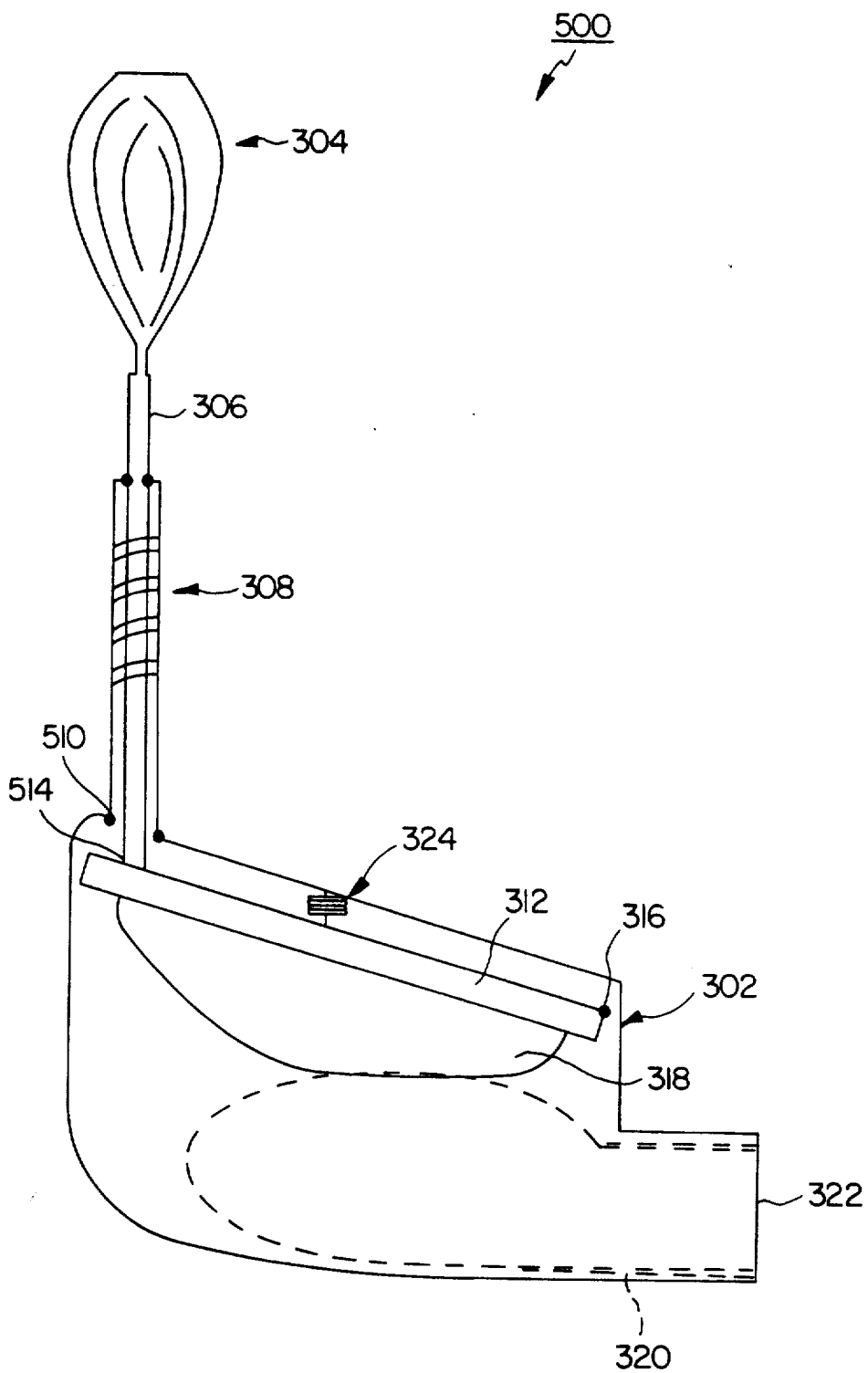
FIG. 5 is a side view of a second version of the second embodiment of the present-inventive cardiac assist device during cardiac systole.
Figure 6:
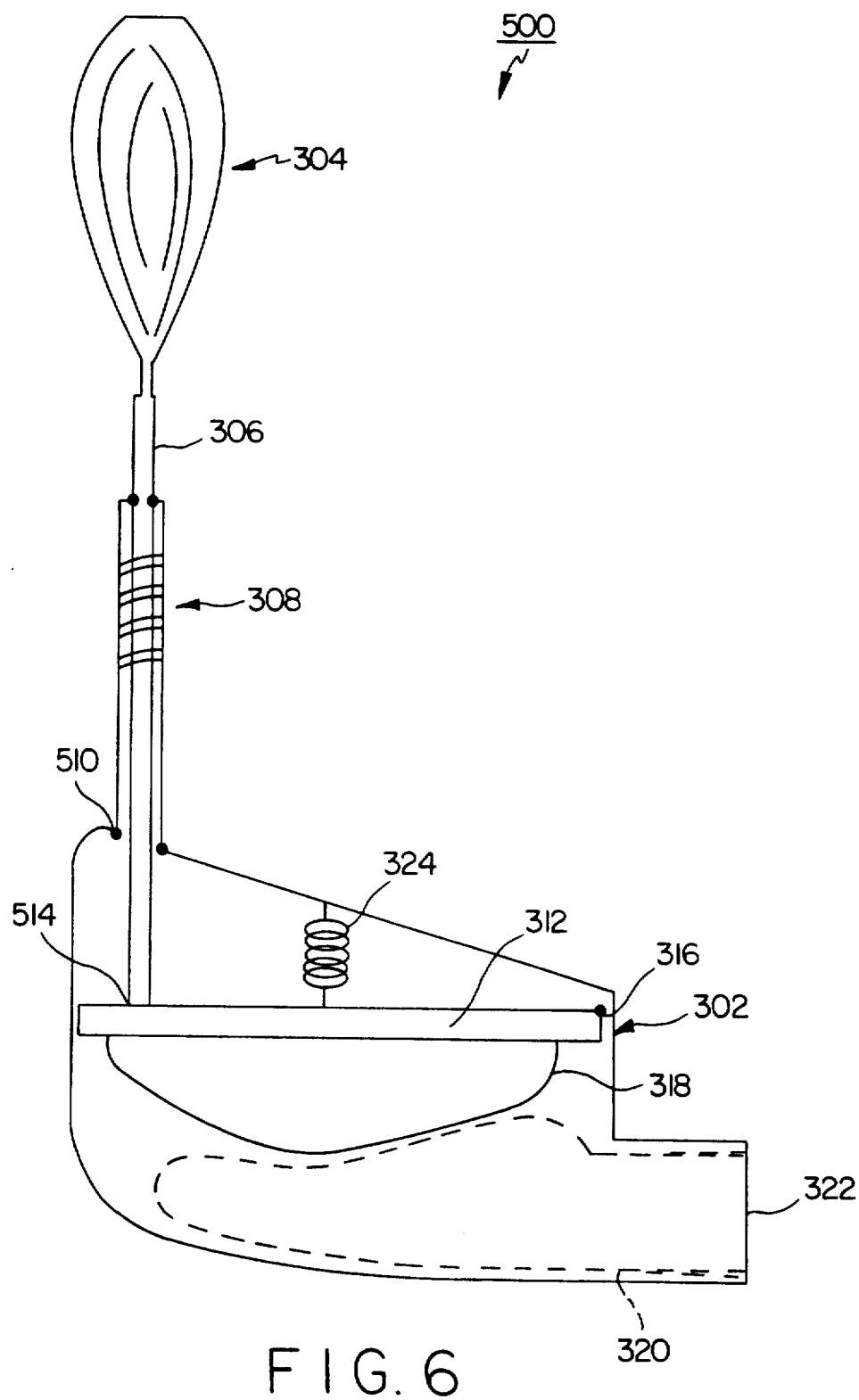
FIG. 6 is a side view of a second version of the second embodiment of the present-inventive cardiac assist device during cardiac diastole.

FIGS. 5 and 6 are second versions 500 of the second embodiment of the cardiac assist device of the present invention during cardiac systole and cardiac diastole, respectively. The cardiac assist device 500 functions identically to the cardiac assist device 300, with a few exceptions. The connecting member 306 is inserted through the wall of the housing 302 from above at an opening 510 (in contrast to insertion from below at opening 310 in FIGS. 3 and 4), and is attached at a hinged point 514 on top of the swivel plate 312 (in contrast to attachment from below the swivel plate 312 at the point 314 in FIGS. 3 and 4).

As a result of the opposite connection of the member 306 and the relative location of the powering muscle tissue 304 in FIGS. 5 and 6, the powering muscle tissue 304 is stimulated to contract during cardiac systole, and is allowed to relax during cardiac diastole (the opposite of the embodiment 300 in FIGS. 3 and 4). During cardiac systole (FIG. 5) the contracted powering muscle tissue 304 pulls up the swivel plate 312 (via the connecting member 306) and hence the compression member 318 to allow the diaphragm to fill with working fluid. At the same time, the return spring 324 is compressed to store potential energy.

When the powering muscle tissue 304 relaxes during cardiac diastole (FIG. 6) the action of the return spring 324 forces the swivel plate downward to cause the compression member 318 to compress the diaphragm 320.

FIG. 7 shows yet a third embodiment of a cardiac assist device 700 optimized for use with the latissimus dorsi muscle. (Recall that the present invention uses the linear motion of the powering muscle, so that the powering muscle need not be limited to the latissimus dorsi.) Most of the components are identical to the components in the cardiac assist devices 300 and 500 in FIGS. 3, 4, 5 and 6. The differences are as follows.

The extension section 708 of the cardiac assist device 700 is elbow-shaped, and may be inserted between two skeletal ribs 728 to secure the device 700 in place. The connecting member 706 is flexible, protrudes through an opening 710 in the housing 302, and connects to the swivel plate 302 at a hinge point 714. The flexible connecting member 706 is diverted by a pulley 726, which allows the more or less horizontal resulting force of the latissimus dorsi muscle tissue 704 to be converted to act on the swivel plate in the vertical direction. It follows from FIG. 7 that the latissimus dorsi muscle 704 contracts during cardiac diastole, and relaxes during cardiac systole (the condition depicted in FIG. 7). The cardiac assist device 700 is thus similar in operation to the cardiac assist device 200, described supra.

In contrast to the first embodiment of the present invention, all versions of the second embodiment of the present invention are optimally designed to be mounted inside of the chest cavity and pump blood directly—although they could be modified to be mounted external to the body and pump a working fluid other than blood.

Variations and modifications to the present invention may be possible given the above disclosure. However, all such variations and modifications are intended to be within the scope of the invention claimed by this letters patent. For example, the present invention is not limited to use with cardiac assist devices, but can be used with assist devices in general, such as devices useful in the treatment of fecal or urinary incontinence, to name a few.

The present invention can operate as either a copulsation device (i.e., it pumps working fluid during cardiac systole), or as a counterpulsation device (i.e., it pumps working fluid during cardiac diastole) with appropriate timing of the muscle tissue stimulation.

The return spring 324 of second embodiment of the cardiac assist device is optional. Where it is included, however, it need not be limited to an actual spring, but may be any suitable return device.

We claim:

1. A muscle-powered cardiac assist device for use in a cardiac assist system, said cardiac assist device comprising:
  a flexible fluid chamber having working fluid therein;
  fluid chamber support means for supporting said flexible fluid chamber;

fluid chamber contraction means coupled to said flexible fluid chamber and to said fluid chamber support means for contracting said flexible fluid chamber to pump said working fluid and further power said cardiac assist system; and linear muscle coupling means for coupling powering muscle tissue to said fluid chamber contraction means, so that substantially linear motion of said powering muscle tissue powers said fluid chamber contraction means;

said linear muscle coupling means comprising force direction changing means for substantially changing the direction of the resulting force imparted by said powering muscle tissue to said fluid chamber contraction means.

2. The muscle-powered cardiac assist device in claim 1 further comprising:

a return mechanism coupled to said fluid chamber contraction means for substantially returning said fluid chamber contraction means to its position prior to contracting said fluid chamber.

3. The muscle-powered cardiac assist device in claim 1 wherein said fluid chamber contraction means contracts said fluid chamber when said powering muscle tissue contracts, and said fluid chamber contraction means allows said fluid chamber to expand when said powering muscle tissue relaxes.

4. A muscle-powered cardiac assist device for use in a cardiac assist system, said cardiac assist device comprising:

a flexible fluid chamber having working fluid therein;
fluid chamber support means for supporting said flexible fluid chamber;
fluid chamber contraction means coupled to said flexible fluid chamber and to said fluid chamber support means for contracting said flexible fluid chamber to pump said working fluid and further power said cardiac assist system; and
linear muscle coupling means for coupling powering muscle tissue to said fluid chamber contraction means, so that substantially linear motion of said powering muscle tissue powers said fluid chamber contraction means;

wherein said working fluid is blood.

5. A muscle-powered cardiac assist device for use in a cardiac assist system, said cardiac assist device comprising:

a flexible fluid chamber having working fluid therein;
fluid chamber support means for supporting said flexible fluid chamber;
fluid chamber contraction means coupled to said flexible fluid chamber and to said fluid chamber support means for contracting said flexible fluid chamber to pump said working fluid and further power said cardiac assist system; and
linear muscle coupling means for coupling powering muscle tissue to said fluid chamber contraction means, so that substantially linear motion of said powering muscle tissue powers said fluid chamber contraction means;
wherein said fluid chamber contraction means contracts said fluid chamber when said powering muscle tissue relaxes, and said fluid chamber contraction means allows said fluid chamber to expand when said powering muscle tissue contracts.

6. A muscle-powered cardiac assist device for use in a cardiac assist system, said cardiac assist device comprising:

a flexible fluid chamber having working fluid therein;
fluid chamber support means for supporting said flexible fluid chamber;
fluid chamber contraction means coupled to said flexible fluid chamber and to said fluid chamber support means for contracting said flexible fluid chamber to pump said working fluid and further power said cardiac assist system; and
linear muscle coupling means for coupling powering muscle tissue to said fluid chamber contraction means, so that substantially linear motion of said powering muscle tissue powers said fluid chamber contraction means;
wherein said fluid chamber contraction means further comprises a cam-shaped compression surface for impacting said fluid chamber during contraction of said fluid chamber.

* * * * *